US005780857A

United States Patent [19]
Harju et al.

[11] Patent Number: 5,780,857
[45] Date of Patent: Jul. 14, 1998

[54] APPARATUS FOR IMAGING BIOCHEMICAL SAMPLES ON SUBSTRATES

[75] Inventors: Raimo Harju, Turku; Mikko Väisälä, Piikkiö, both of Finland

[73] Assignee: Wallac Oy, Turku, Finland

[21] Appl. No.: 726,467

[22] Filed: Oct. 4, 1996

[51] Int. Cl.[6] .................................................. G03B 42/00
[52] U.S. Cl. ........................................ 250/458.1; 250/583
[58] Field of Search ............................ 250/458.1, 583, 250/584, 585

[56] References Cited

U.S. PATENT DOCUMENTS 5,528,050   6/1996   Miller et al. ..................... 250/458.1

*Primary Examiner*—Don Wong
*Attorney, Agent, or Firm*—Kubovcik & Kubovcik

[57] ABSTRACT

A multi-purpose optical scanner that is provided for performing different type of high sensitivity imaging of planar biochemical samples. These types of samples include stimulable phosphor image plates, fluorescently labelled samples like electrophoretic gels, TLC-plates, blots etc. or multi-well support of samples and colored planar samples. According to an embodiment of the present invention the multi-purpose optical scanner comprises a measurement unit, a sample support and a scanning mechanics to provide relative movements between the sample on the sample support and the measurement unit. The measurement unit includes a fiber-coupled light source and a measuring head having a fixed light source, a detector, optics and a holder for interchangeable and application specifics filter cubes. The filter cubes include necessary filters and beamsplitters for different operating modes and applications. The orientation of the beamsplitter in the specific filter cube determines which light source will be in use.

24 Claims, 2 Drawing Sheets

APPARATUS FOR IMAGING BIOCHEMICAL SAMPLES ON SUBSTRATES

BACKGROUND OF THE INVENTION

1. Field of the Invention

The present invention relates generally to optical scanners and more particularly to a scanner type apparatus for imaging different biochemical samples distributed on flat supports i.e. chromatographic and electrophoretic patterns for visualization and computer analysis.

2. Description of Prior Art

In many biochemical methods of separation and analysis the distribution and quantity of various proteins or other molecules on a plane type base will be measured. Typical examples of such methods are gel electrophoresis and planar chromatography. More recent methods are, for example, hybridization's and various kinds of cell separation methods carried out on filter materials.

Detecting for few molecules as such on a given surface is extremely difficult. In biochemistry the substances examined must be labelled with a label or a tracer to facilitate identification or detection.

Until the past decade, various radioactive labels have been practically the only type of the labels used, and still today a large number of routine research is carried out with isotopic labels. Only in recent years have various non-isotopic labels, like chemiluminescent and fluorescent labels been adopted more widely for use.

The detection of two-dimensional distribution of radioactive labels is most often performed by contact imaging with photographic film. This method is called autoradiography. During the last five years the film has been partly substituted by a special ceramic-coated plate called photo-stimulable phosphor image plate. These plates have been exposed like a film but image of the stored radiation have been read out with a special scanner. Some of these instruments are disclosed for example in the following U.S. Pat. Nos. 3,859,527; 4,258,264; 4,302,671 and 4,346,295. Typically the most modern commercial phosphor image plate scanners are using red laser beam, which is scanned with an oscillating mirror and it is focused into a flat surface with a special scan lens also called theta-lens. The consequent near-ultra-violet light emission will be collected and conducted to the detector with a bundle of fibers or with a special plastic light guide.

There is also available a different phosphor image plate readout device which uses scanning optical probe technology. In this instrument both the stimulating light and the emission light will be conducted via optical fiber and the excitation is focused onto the sample surface using so called GRIN-lens. This instrument is disclosed in U.S. Pat. No. 5,266,803.

The fluorescence and the fluorescent labels have been used quite many years in planar chromatography and these samples have been read with different type of scanning fluorescent densitometers, one example is disclosed in U.S. Pat. No. 4,117,338.

However, the main interest here is the gel electrophoresis with fluorescent labels. Scanning fluorescent densitometers are also capable to read fluorescent labelled gels, but they have not been used much there probably due to their low sensitivity, low resolution and slow scanning speed. Most of the fluorescent work with gels have been utilized ethidium bromide labelling and visual inspection or Polaroid film documentation on top of UV-light box. Polaroid film cameras have been replaced now by low noise solid state video cameras and video printers.

If the question is of the quantitative determination of protein with fluorescent labels the above described methods are not sufficient. For quantitative purposes the sophisticated high resolution fluorescent scanner has been commercialized by Molecular Dynamics and disclosed in U.S. Pat. No. 5,424,841. Another same type instrument is commercialized by Hitachi Software Engineering Co. and its features are disclosed in U.S. Pat. No. 5,190,632.

Although these instruments have been basically constructed by the same way as the phosphor image plate scanners, utilizing laser beam scanning, these instruments were not easily adopted for phosphor image plate reading. The excitation wavelength of fluorescence scanners differ so much from the stimulation wavelength of phosphor image plate scanners that the laser itself and also many other optical components had to be changed. It means that to build a combine instrument utilizing laser beam scanning would be expensive and impractical.

In U.S. Pat. No. 5,091,652 (Mathies et al) there is disclosed a laser excited confocal fluorescent scanner and a method. The confocal principle was adopted from microscopes to the gel scanning. They did achieve good resolution and high sensitivity but its realization was mechanically very demanding in large sample sizes like 200 mm * 250 mm due to the small working distance, the small image depth. Also the practical gels are often only few millimeters thick and their surface is uneven.

In a slightly different field of automated DNA-sequencers there have been utilized also various gel scanners. There the gels will be read during the separation process itself, thus the measuring probe needs to move only in one direction. The excitation light is often supplied in to the moving probe using mirrors moving in collimated laser beam. Two of these instruments have been disclosed in U.S. Pat. Nos. 4,811,218 (Hunkapiller et al.) and 5,100,529 (Fujii).

The same principle is applied in the high speed fluorescence scanner disclosed in U.S. Pat. No. 5,459,325 (Hueton et al.). However, this principle performs well only with collimated laser beam and in relative short distances between the excitation source and scan head.

The reading of molecular fluorescence and the reading of stimulated phosphorescence are the same type of measurement methods and they have been used for the same analytical purposes in the same laboratories. Therefore it would be an advantage if these measurements could be performed with the same instrument, the output image files would be of the same type and different methods could be easily compared.

OBJECTS AND SUMMARY OF THE INVENTION

It is therefore an object of the present invention to provide a compact multi-purpose apparatus for quantitative reading of different types of flat samples in the field of biochemistry. These type of samples include for example:

- phosphor image plates capable of storing radiation image information from isotope labelled gels, blots, TLC-plates etc.,
- fluorescent labelled gels, filters etc., regardless of the type of the labels whether they are based on the classical molecular fluorescence or the time-resolved luminescence,
- microtitration plates with fluorescent samples, colored planar samples.

These objects can be accomplished by providing an apparatus for reading optical emission or reflection intensities from stimulated phosphor image plates, excited fluorescently labelled samples or colometricly labelled samples. The apparatus is comprising:

a measurement unit, a sample support plate, means for performing relative movement between the measuring head and the sample on the sample support.

The measurement unit is comprising:

a fiber coupled light source allowing excitation of broad selection of fluorescent labels. Preferable it is a xenon arc point source, equipped with a chopper for millisecond region time-resolved applications or a pulsed xenon source for more demanding time-resolved applications, and a measurement head.

The measurement head is comprising:

a fixed light source preferably a semiconductor laser for stimulation of phosphor image plates or fluorescence excitation of suitable red or near-infrared fluorochromes, another optical input located on the opposite side of the fixed light source, an objective lens for focusing incident light and for collecting emitted or reflected light from the sample, a holder for interchangeable filter cubes and a set of different filter cubes, a sensitive detector preferably a head-on photomultiplier, and detection electronics including linear amplifier, analogue-to-digital converter and the computer interface.

DETAILED DESCRIPTION OF THE PREFERRED EMBODIMENT

Figure 1:
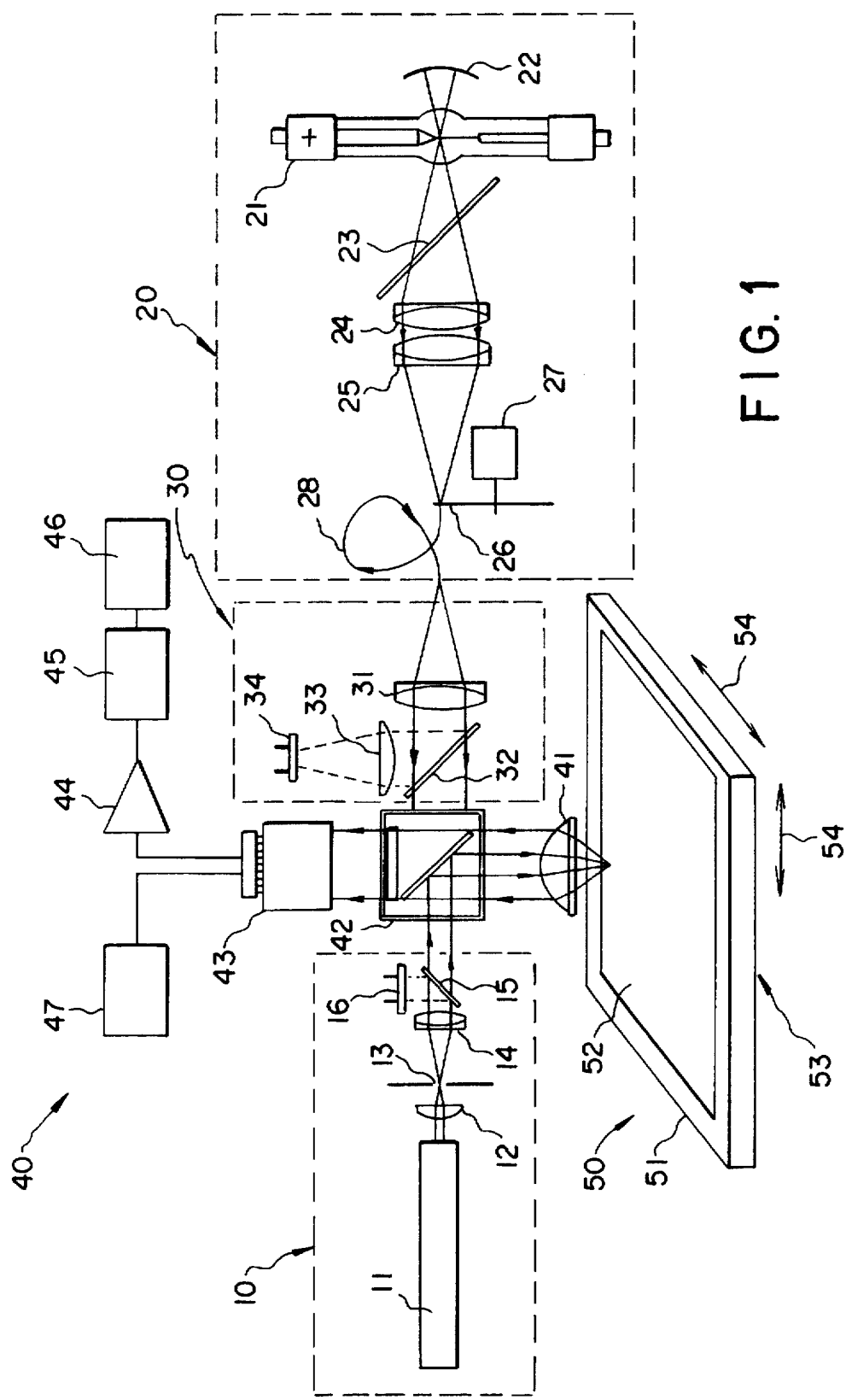
FIG. 1 shows a preferred embodiment of the multi-purpose optical scanner.

FIG. 1 shows a preferred embodiment of the multi-purpose optical scanner. The preferred embodiment of the present invention in FIG. 1 comprises following units: a measurement head comprising a fixed light source unit 10, fiber input unit 30 and the emission unit 40, the fiber-coupled light source 20 and a sample compartment 50 including the scanning mechanism.

The fixed light source unit 10 has a small collimated semiconductor laser 11 as a light source with wavelength about 630–670 nm. A lens 12 focuses the laser beam in to a pinhole 13. An achromatic lens 14 collimates the light from the pinhole 13 through a beamsplitter 15 in to an emission unit 40. The beamsplitter 15 reflects a small portion of the light into a reference photodiode 16. The output of the reference photodiode 16 is used to stabilize the optical power of the laser 11. The electronics of the system is not shown.

The fiber coupled light source 20 has a broad band discharge light source 21, preferably DC xenon short arc lamp, a spherical back reflector 22 to gain more effective light collection, a hot mirror 23 for reflecting infrared energy out of the beam, achromatic lenses 24 and 25 to collect the light from lamp and to focus the light into an optical fiber 28. In the vicinity of the input aperture of the fiber there is located a chopper plate 26 rotated by a motor 17. The optical fiber 28 isolates mechanically and thermally the bulky high power discharge light source from the measurement head. A fiber input unit 30 comprises a lens 31 that collimates the light from fiber 28 through a beamsplitter 32 into an emission unit 40. The beamsplitter 32 reflects a small portion of the light through a lens 33 which focuses the light into a reference photodiode 34. The output of the reference photodiode 34 is used to stabilize the optical power of the arc source 21. The electronics is not shown.

The emission unit 40 comprises a large numerical aperture objective lens 41 which in this embodiment is simple glass aspheric lens, a filter cube holder 42, a detector 43, which could be of a small modern metal-can type photomultiplier, a linear amplifier 44, an analogue-to-digital converter 45 and a computer interface card 46. The high voltage for the photomultiplier is supplied by a power supply 47.

The sample compartment 50 includes a sample support plate 51 and a sample 52. Below the sample support plate 51 there is a scanning mechanism 53, not shown in FIG. The double arrows 54 show the orthogonal scanning directions.

The filter cube used inside the filter holder 42 are application dependent and basic types of different filter cubes are shown in FIGS. 2–5.

Figure 2:
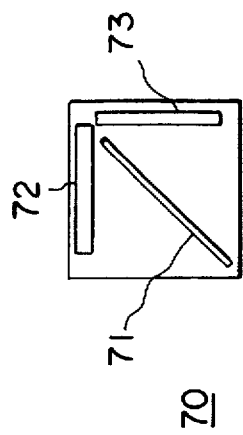
FIG. 2 shows a configuration of the filter cube used in phosphor image plate reading mode.

FIG. 2 shows a filter-cube 60 which is used when measuring phosphor image plates. This filter cube comprises dichroic mirror 61 and emission filter 62. The dichroic mirror 62 is tilted 45 degrees towards the beam coming from the fixed light source and it reflects the light downward into the input aperture of the objective lens.

Figure 3:
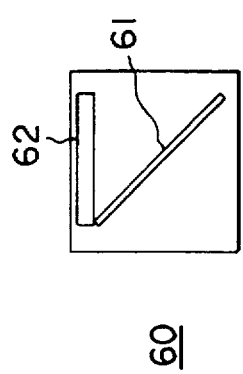
FIG. 3 shows a configuration of the filter cube for fluorescence reading mode.

FIG. 3 shows a filter-cube 70 which is used in most typical fluorescence application. This filter cube comprises dichroic mirror 71 and emission filter 72 and excitation filter 73. The dichroic mirror 71 is not tilted 45 degrees towards the beam coming from the filter input unit 30 it reflects the light downward into the input aperture of the objective lens 41. There is needed a different filter-mirror combination for different fluorescent labels with different spectral characteristics.

Figure 4:
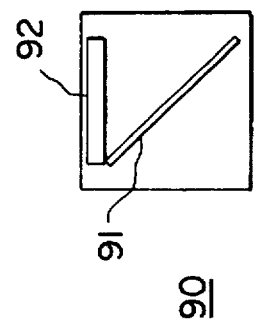
FIG. 4 shows a configuration of the filter cube for reading mode of colored plate samples.

FIG. 4 shows a filter-cube 80 which is used when reading colored plates common in thin-layer chromatography. This filter cube comprises non-dichroic beamsplitter mirror 81 and bandpass filter 83 to choose desired absorptive wavelength to the reflection measurement. Mirror 81 is tilted 45 degrees towards the beam coming from the fiber input and it reflects a portion of the light downward into the input aperture of the objective lens. The objective focuses the light on to the sample and it is partly absorbed and partly reflected depending on the concentration of stain on TLC-plate.

Figure 5:
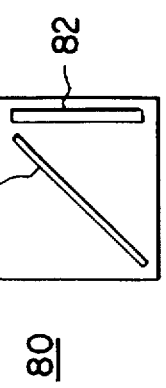
FIG. 5 shows a configuration of the filter cube for infrared fluorescence reading mode.

FIG. 5 shows a filter-cube 90 which is used at certain infrared fluorescence application. This filter cube comprises dichroic mirror 91 and emission filter 92. The dichroic mirror 91 is not tilted 45 degrees towards the beam coming from the semiconductor laser and it reflect the light downward into the input aperture of the objective lens 41. No excitation filter is needed as the semiconductor laser light is enough monochromatic. There is needed a different filter-mirror combination for other fluorescent labels with different spectral characteristics.

Description will now be made of a process in which the multi-purpose scanner, as herein above described, is used to form image of different types of samples.

Phosphor image plate reading

Phosphor image plate reading is performed using the fixed light source unit 10 and related filter cube 60. Most common used phosphor image plates are stimulated by red light and consequent luminescence is at the blue and near ultraviolet (360–460 nm) region of the spectrum. The collimated beam of 1.5 mW laser diode 11 of wavelength 670 nm is focuses with plano-convex glass lens 12 in to the pinhole 13 of the diameter of 100 micrometers. The laser beam out of pinhole 13 is collimated with anti-reflection coated achromatic lens 14 (f=25 mm) and this collimated beam is reflected downwards with the mirror 61 located in the filtercube 60. Mirror 61 is a dichroic mirror, where red light is reflected and blue light transmitted.

The objective lens 41, in this embodiment a standard anti-reflection coated aspheric lens of focal length 18 mm, is focusing the beam on to the surface of the sample 52. The spot size on the phosphor image plate is about the size of the pinhole. The amplified output from reference photo diode 16 is fed to the power supply of the laser diode for stabilization purposes. The stabilization of the laser when reading phosphor image plates is extremely important because the fluctuations of the laser power are difficult to compensate in reading results due the unlinear relation between emission and stimulation.

The whole phosphor image plate is scanned with this spot line by line. Typical phosphor image plate size is 250×200 mm and if the scanning resolution is five lines/mm, totally 1000 lines have to be scanned to form a whole image. Highest reasonable scanning speeds with ball-screws are about 0.5 m/s and with stops and turns and accelerations outside the sample area the reading of one line takes about one second.

The blue emission light from stimulated phosphorescence crystals of the phosphor image plate is collected with high numerical aperture aspheric objective lens 41. This lens has multi-layer antireflection coating which is optimized at the region of the laser wavelength. In phosphor image plate scanner most of stimulation light is scattered out of the phosphor image plate surface and this scattered light have to be absorbed somewhere, so that it cannot get back again on to the surface of phosphor image plate. The scattered stimulation light would erase the phosphor image plate and information of the part of the plate would be lost.

The objective lens 41 collimates the emission light through the emission filter 61 in the filter cube 60 in to the detector 43. Because the amount of scattered stimulation light is much bigger than the real signal the emission filter 61 in the filter cube 60, has critical demands. It should attenuate the read stimulation light about two magnitudes but should have a good transmission for blue emission light. The glued stack of color filter glasses have a good blocking characteristics for stimulation light but its transmission is only about 30% for emission light. The specially designed thin film short pass filter combined with absorptive glass, is far more effective.

Because the emission light levels from stimulated phosphor image plates are low the photomultipliers are generally used as detectors 43 in phosphor image plate scanners. The simulation light of wavelength of 670 nm has extra advantage with certain photomultipliers that the photo-electric converter layer of photomultiplier tube, photocathode, has best sensitivity on the blue region of the optical spectrum and very poor sensitivity at the wavelength of 670 nm thus helping the filter design.

If the pixel size is square there is 1250 readings or pixels in one line, which make A/D-conversion frequency of 2500 Hz. Due the large inherent dynamic range of phosphor image plate there is needed a 16-bit A/D-conversion. Thus the image file size is 2.5 Mbytes. Images are analyses in PC with a separate program.

Fluorescence reading

As a simple molecular process the fluorescence emission is stimulated or excited at lower wavelength light than subsequent emission. Also there is available a huge number of fluorescent labels with different emission and excitation wavelengths. One group of labels which use is increasing, are the so called infra-red (IR) labels. These labels are excited at the red end of the visible spectrum and their emission wavelengths are at the near-infrared or region electromagnetic spectrum. Very often read laser diodes are capable to excite IR-labels. For this reason the described embodiment (FIG. 1) of the invention is capable to image certain IR-fluorescence label using filter cube 90. In this also the detector 43 must be near-infrared sensitive which has some disadvantages in phosphor image plate reading.

However most fluorescent labels in molecular biology are excited in the ultra-violet, blue or green region of the optical spectrum. Most flexible and effective excitation sources for these labels are different type of short arc discharge lamp, both flash type or continuous wave type. But because these lamps are often bulky and generate extra heat they are most suitable for fiber optic coupling. This kind of embodiment is shown as a part in FIG. 1, but now must use filter cube 70.

One common fluorescent label is fluorescein and its derivatives, which excitation and emission wavelength are 490 and 515 nm, respectively. The excitation light from arc lamp 21 is collected and collimated with mirror 22 and a lens 24 then light is focused with a lens 25 into the optical fiber 28. The fiber output is collimated into the dichroic mirror 71 in the filter cube 70. The mirror 71 directs the excitation light downwards in to the objective 41. The reference beamsplitter 32, a thin uncoated glass plate reflects about 8% of the beam into the lens 33 which focuses the reference beam on to the surface of the photo-diode 34. With arc sources, due small arc wandering, it is important that the whole beam is probed for reference. The output of amplified reference signal is used to stabilize the arc source output. If the used excitation source is difficult to stabilize the reference output can also be used for correction of the fluorescence signal, if fluorescence is measured in the linear region of the label. The dichroic mirror 71 must be specially designed for each label, so that it reflects excitation wavelength but transmits emission wavelengths. Also the emission filter 73 must be specially designed band-pass filter for the label to achieve good enough signal-to-noise ratio of the measurements.

If the label is excited at ultra-violet region of optical spectrum transmission properties of the whole optical excitation path must be carefully considered. Often the optical component must be high-purity synthetic fused silica to avoid background fluorescence from component itself and to allow good transmission properties.

If the label used is so called time-resolved, for example europium-chelate, its unique properties could be utilized using optical chopper plate 26 with continuous lamp or a flash lamp (not shown). The decay times of lanthanide chelates are typically from 100 μs to few milliseconds. When decay times are at that region the time-resolved measurements are easily accomplished by chopping excitation light mechanically and delaying reading after excitation pulse for a certain time. Above mentioned scanning speeds would allow only one excitation pulse per pixel and chopping frequency of 2.5 kHz. In this case the decay time of the label would affect resolution in direction of scanning line.

In some application the whole fiber coupled light source could be change fiber coupled laser, if the excitation band matches the laser line. The laser have advantage of getting higher excitation powers into smaller fiber. Smaller fibers means overall better possible resolution and high power allows higher scanning speeds.

However, what is not shown here, it is also common practice, for example in flow cytometers, to use two more detectors with application specific dichroic mirrors allowing the detection of two or more fluorescent labels every with characteristic spectral properties.

Colored plate samples

Reflection mode allows the multi-purpose scanner to analyze also stained thin-layer chromatography plates and for instance silver-stained electrophoretic gels. The fiber coupled light source 21 can be used for reflective measurement with a filter cube 80. The broad band light from source 21 is collected with a lens 24 and focused with lens 25 into the optical fiber. The from other end of the fiber light is collimated with the lens 31 into the mirror 81 in the filter cube 80 which is now located in the filter cube holder 42 of the emission unit 40. The mirror 81 directs the light downward and the lens 41 focuses it on to the sample surface 52. Depending on the surface absorption properties variable amounts of light is reflected out of surface, from which a certain share is collected by the lens. There is no need for any emission filter because the is no background light to filter presuming the light shield box is tight. In any case the design opto-mechanics components and optical coating have to do carefully to avoid any internal reflection inside the instrument itself.

The whole plate is scanned with light spot and amounts reflected light is recorded pixel by pixel. These values can be converted using known equation for absorption values which are linearly related to the concentration of the stain in the sample.

There is another embodiment according to this invention where the sample is moving only one direction performing only one-dimensional scan and the measuring head itself is performing the scan which is orthogonal against the first one. Relative small measurement head could be easily moved back and forth with frequency of 1 or 2 Hz. In this embodiment the programmable automatic changer of filter cubes could be easily arranged. The cube not in use at the moment could be located in a rateable carousel, from where a new filter cube could be picked when needed. The cube can also be a part of a slide unit.

Although the invention has been described with reference to the phosphor image plate or electrophoretic gels, it is equally applicable to any form of sample matrix like multiwell plates etc.

The invention has been described with reference to a preferred embodiments. It is to be understood that variations or modifications may be easily made by anybody of ordinary skill in the art without departing from the scope of this invention which is defined by the appended claims.

What is claimed is:

1. A method of quantitative reading of different types of flat samples by an imaging apparatus of optical scanner type, which samples include such components as phosphor image plates, fluorescent labelled gels and filters, microtitration plates with fluorescent samples and colored planar samples, the method comprising the following steps:

placing the sample on the sample support in the multi-purpose optical scanner, installing an appropriate filter cube into the filter cube holder of the multi-purpose optical scanner, switching on the appropriate light source, scanning the sample line by line, collecting the subsequent optical signal into the photodetector, sensing the photodetector output with appropriate electronics, saving the output signal into the memory of the computer for later analysis.

2. An imaging apparatus of an optical scanner type for measuring biochemical samples on substrates, the apparatus being a multipurpose optical scanner to operate in a measurement mode selected from phosphor image plate reading, fluorescence reading or colored plate sample reading; the apparatus comprising:

a sample support plate supporting a sample, a measurement head being movable to scan the sample, a light source being a remote light source equipped with an optical guiding means for guiding light from the light source to the measurement head;

said measurement head having a detector being connected to detection electronics with a computer interface, and an objective lens being adapted for focusing stimulating light from the light source on to the sample and for collecting light emitted from the sample into the detector, which emitted light is caused by the stimulating light;

wherein in the imaging apparatus said measurement head comprises a holder for an interchangeable optical part, the holder having mechanical attachments and optical paths for the interchangeable optical part, in the holder of said measurement head is placed one interchangeable optical part, said interchangeable optical part comprising corresponding mechanical attachments and optical paths for the mechanical attachments and the optical paths of the holder, a specific combination of optical components to determine the imaging apparatus for operating a specific measurement mode, and said apparatus having means for storing interchangeable optical parts.

3. An imaging apparatus of claim 2 where said remote light source is a laser.

4. An imaging apparatus of claim 3 where said laser of the remote light source is a continuous wave laser.

5. An imaging apparatus of claim 4 where said continuous wave laser of the remote light source is equipped with an optical chopper.

6. An imaging apparatus of claim 3 where said laser of the remote light source is of pulsed type.

7. An imaging apparatus of claim 2 comprising said measurement head and at least two mutually interchangeable parts which are filter cubes.

8. An imaging apparatus of claim 7 where said set of filter cubes includes at least two different cubes.

9. An imaging apparatus of claim 2 wherein the remote light source is a short arc discharge lamp, which is a continuous wave lamp or a pulsed lamp.

10. An imaging apparatus of claim 9 where said continuous wave short arc discharge lamp of the remote light source is equipped with an optical chopper.

11. An imaging apparatus of claim 9 further comprising an optical input includes a reference photodiode.

12. An imaging apparatus of claim 9 where said objective lens is a single aspheric lens.

13. An imaging apparatus of claim 12 where said aspheric lens is coated with an anti-reflection coating optimized at the stimulation wavelength of the phosphor image plates.

14. An imaging apparatus of claim 2 wherein one of said interchangeable optical parts is a filter cube for fluorescence reading, said filter cube comprising an excitation filter, a dichroic mirror which reflects at least excitation light, and an emission filter.

15. An imaging apparatus of claim 2 wherein said means for the sample support comprises an one-dimensional translator located under the sample support plate and a second translator for moving said measurement head orthogonal to the sample support direction.

16. An imaging apparatus of the optical scanner type for measuring biochemical samples on substrates, the apparatus being a multipurpose optical scanner to operate in a measurement mode selected from phosphor image plate reading, fluorescence reading or colored plate sample reading, and the apparatus comprising:

a sample support plate supporting a sample, a measurement head being movable to scan the sample, a first light source being a remote light source equipped with an optical guiding means for guiding light from the first light source to the measurement head, the measurement head having a detector being connected to detection electronics with a computer interface, wherein in the imaging apparatus said measurement head comprises a fixed light source, an objecting lens being adapted for focusing stimulating light from the first light source on to the second light source onto the sample and for collecting light emitted from the sample into the detector, which emitted light is caused by the stimulating light;

a holder for an interchangeable optical part, the holder having mechanical attachments and optical paths for the interchangeable optical part, in the holder of said measurement head is placed one interchangeable optical part, said interchangeable optical part comprising corresponding mechanical attachments and optical paths for the mechanical attachments and the optical paths of the holder, a specific combination of optical components to determine the imaging apparatus for operating a specific measurement mode, and said apparatus having means for storing interchangeable optical parts.

17. An imaging apparatus of claim 16 wherein the said second light source is a semiconductor laser.

18. An imaging apparatus of claim 17 where said second light source of said measurement head is a frequency doubled or tripled semiconductor laser.

19. An imaging apparatus of claim 16 wherein one of said interchangeable optical parts is a filter cube for phosphor image plate reading, said filter cube comprising a dichroic mirror which reflects stimulating light from the second light source and transmits a subsequent emission from the plate, and an emission filter which absorbs scattered stimulation light and is transmissive for emission from the plate.

20. An imaging apparatus of claim 16 wherein one of said interchangeable optical parts is a filter cube for near infrared fluorescence reading, said filter cube comprising a dichroic mirror which reflects exciting light from the second light source and transmits a subsequent emission from the plate, and an emission filter which absorbs scattered stimulation light and is transmissive for emission from the plate.

21. An imaging apparatus of claim 2 or 16, wherein the optical guiding means for the light source is an optical fiber.

22. An imaging apparatus of claim 2 or 16, wherein said means for storing interchangeable optical parts is a rotatable carousel outside the measuring head or a slide unit outside the measuring head.

23. An imaging apparatus of claim 2 further comprising means for providing relative movement between said measuring head and the sample on the sample support and comprising an x-y-table located under the sample support plate.

24. An imaging apparatus of claim 21 where one of said interchangeable optical parts is a filter cube for colored plate reading, said filter cube comprising a filter which selects a needed wavelength for probing absorptive properties of the sample, and a beamsplitter mirror which partially reflects probing light from the light source and partially transmits reflected and scattered probing light from the sample plate.

* * * * *